United States Patent
Isshiki

(10) Patent No.: US 12,295,566 B2
(45) Date of Patent: May 13, 2025

(54) CLEATING SYSTEM FOR A MEDICAL CANNULA

(71) Applicant: Conmed Corporation, Largo, FL (US)

(72) Inventor: Ryo Isshiki, Largo, FL (US)

(73) Assignee: Conmed Corporation, Largo, FL (US)

( * ) Notice: Subject to any disclaimer, the term of this patent is extended or adjusted under 35 U.S.C. 154(b) by 644 days.

(21) Appl. No.: 17/765,102

(22) PCT Filed: Oct. 5, 2020

(86) PCT No.: PCT/US2020/054250
§ 371 (c)(1),
(2) Date: Mar. 30, 2022

(87) PCT Pub. No.: WO2021/067929
PCT Pub. Date: Apr. 8, 2021

(65) Prior Publication Data
US 2022/0338860 A1    Oct. 27, 2022

Related U.S. Application Data

(60) Provisional application No. 62/909,891, filed on Oct. 3, 2019.

(51) Int. Cl.
*A61B 17/04*    (2006.01)
*A61B 17/34*    (2006.01)

(52) U.S. Cl.
CPC ...... *A61B 17/0401* (2013.01); *A61B 17/3462* (2013.01); *A61B 2017/0438* (2013.01); *A61B 2017/044* (2013.01); *A61B 2017/0445* (2013.01)

(58) Field of Classification Search
CPC ...... A61B 2017/0445; A61B 2017/349; A61B 2017/0403; A61B 2017/0404;
(Continued)

(56) References Cited

U.S. PATENT DOCUMENTS

| 5,496,289 A | 3/1996 | Wenstrom, Jr. |
| 7,704,263 B2 | 4/2010 | Morris et al. |

(Continued)

FOREIGN PATENT DOCUMENTS

| JP | H02189163 A | 7/1990 |
| JP | 2003520652 A | 7/2003 |

(Continued)

OTHER PUBLICATIONS

International Search Report Form PCT/ISA/220, International Application No. PCT/US2020/054250, pp. 1-14, Dated Jan. 11, 2021.
(Continued)

*Primary Examiner* — Majid Jamialahmadi
(74) *Attorney, Agent, or Firm* — Bond, Schoeneck & King, PLLC; Frederick J. M. Price

(57) ABSTRACT

A suture cleating system for arthroscopic or endoscopic cannula to facilitate suture management while preserving seal functionality. The suture cleating system includes an end cap with an aperture extending therethrough and one or more cleats extending therefrom. A cannula body extends distally from the end cap. A seal is connected between the cannula body and the end cap. The seal has a seal slit extending therethrough and the seal slit is substantially aligned with the aperture of the end cap. In use, a suture extends through the cannula, the seal slit, and the aperture in the end cap. The suture can be tensioned from the aperture in the end cap and secured in a suture slot between two cleats.

17 Claims, 14 Drawing Sheets

(58) Field of Classification Search
CPC .... A61B 2017/0406; A61B 2017/0408; A61B 2017/0409; A61B 2017/0411; A61B 2017/0412; A61B 2017/0414; A61B 2017/0416; A61B 2017/0417; A61B 2017/0419; A61B 2017/044; A61B 17/0401; A61B 17/06061; A61B 17/3462
See application file for complete search history.

(56) References Cited

U.S. PATENT DOCUMENTS

| | | |
|---|---|---|
| 2005/0065535 A1 | 3/2005 | Morris et al. |
| 2006/0167479 A1 | 7/2006 | Morris et al. |
| 2010/0191261 A1* | 7/2010 | Carter ................ A61B 17/3462 606/150 |
| 2011/0022064 A1 | 1/2011 | Barnes |
| 2012/0089161 A1 | 4/2012 | Lunn et al. |
| 2015/0065808 A1 | 3/2015 | Van Wyk et al. |

FOREIGN PATENT DOCUMENTS

| | | |
|---|---|---|
| JP | 2010527710 A | 8/2010 |
| JP | 2010240421 A | 10/2010 |

OTHER PUBLICATIONS

English Translation of JP Office Action, dated Jun. 2, 2023, App. No. 2022-519564, pp. 1-8.
Translated Chinese First Office Action, App. No. 202080070063.8, dated Nov. 29, 2023, pp. 1-16.

* cited by examiner

CLEATING SYSTEM FOR A MEDICAL CANNULA

CROSS-REFERENCES TO RELATED APPLICATIONS

This application is a national stage application under 35 U.S.C. 371 based on international patent application PCT/US20/54250 filed on Oct. 5, 2020, which claims priority to U.S. Provisional Patent Application Ser. No. 62/909,891, filed on Oct. 3, 2019 and entitled "Cleating System for a Medical Cannula," the entireties of which are incorporated herein by reference.

BACKGROUND OF THE INVENTION

1. Field of the Invention

The present invention relates to a cannula and, more particularly, to a cleating system for an arthroscopic or endoscopic cannula.

2. Description of Related Art

Cannulae may be used to support arthroscopic or endoscopic procedures by providing access portals to a surgical site. To address issues of fluid management, cannulae may be equipped with a seal system at the proximal end. The flexible seal limits fluid flow through the cannula, but also supports access of the surgical site with instruments, implants or sutures.

Over the course of an arthroscopic or endoscopic surgery, multiple sutures may be passed and manipulated through a cannula. Cannulae may be designed to present features such as cleats to facilitate suture management. In the context of an arthroscopic or endoscopic procedure, the section of the suture that is directly accessible to the user is the portion of the suture that has been pulled outside the patient. When performing such a procedure through a cannula, the accessible sections of the suture have been passed through the flexible cannula seal.

To firmly cleat a suture, the suture must be pulled into the cleating feature under tension. Since the midsection of the suture still engages the flexible seal, the cleating of multiple sutures in opposing directions carries the inherent risk of stretching open the flexible seal. This can be observed in FIG. 1, which shows a seal on a cannula of the prior art. The seal is pulled open while cleating multiple sutures. When the flexible seals in a cannula are pulled apart in this manner, the cannula is at a higher risk of fluid leakage and jetting.

Therefore, there exists a need for a suture cleating system for an arthroscopic or endoscopic cannula that does not pull the seal(s) apart during usage.

The term "suture" as used herein may be any type of filamentous material such as a biocompatible or bioabsorbable filament, ribbon, tape, woven or non-woven material.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention are directed to a suture cleating system for an arthroscopic or endoscopic cannula to facilitate suture management while preserving seal functionality. An embodiment of the suture cleating system includes an end cap comprising an outer surface with an aperture extending therethrough and one or more cleats extending therefrom. A seal is connected to the end cap. The seal has a seal slit extending at least partially across its diameter. The seal slit is substantially aligned with the aperture of the end cap.

According to another aspect, the suture cleating system includes an end cap with an aperture extending therethrough and one or more cleats extending therefrom. A cannula body extends distally from the end cap. A seal is connected between the cannula body and the end cap. The seal has a seal slit extending therethrough and the seal slit is substantially aligned with the aperture of the end cap.

In use, a suture extends through the cannula, the seal slit, and the aperture in the end cap. The suture can be tensioned from the aperture in the end cap and secured in a suture slot between two cleats.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 2:
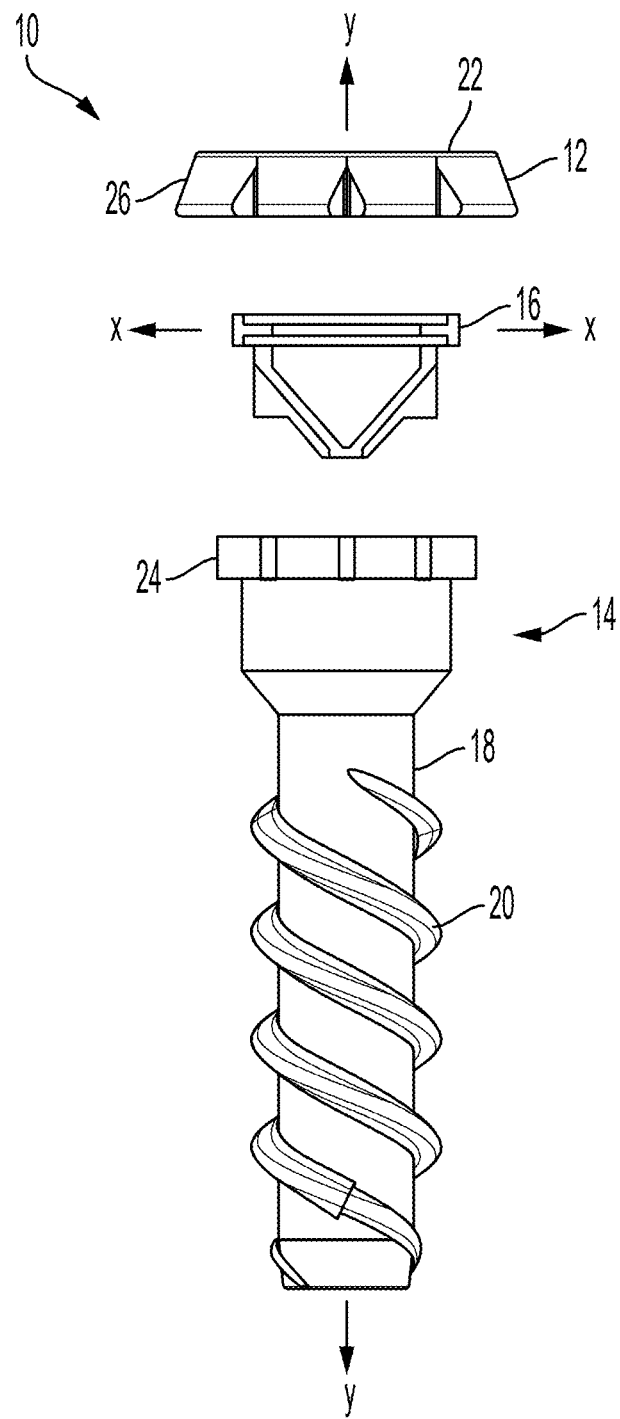
FIG. 2 is a side view of a suture cleating system, according to an embodiment.

Referring now to the figures, wherein like reference numerals refer to like parts throughout, FIG. 2 is a side view of a suture cleating system 10, according to an embodiment. The suture cleating system 10 includes a proximal end cap 12 with a cannula body 14 extending therefrom. A seal 16 is positioned between the end cap 12 and the cannula body 14. The cannula body 14 is a tube 18 with an inner volume (not shown) extending therethrough. As shown in FIG. 2, the cannula body 14 has threads 20 extending along at least a portion of the tube 18.

Figure 3:
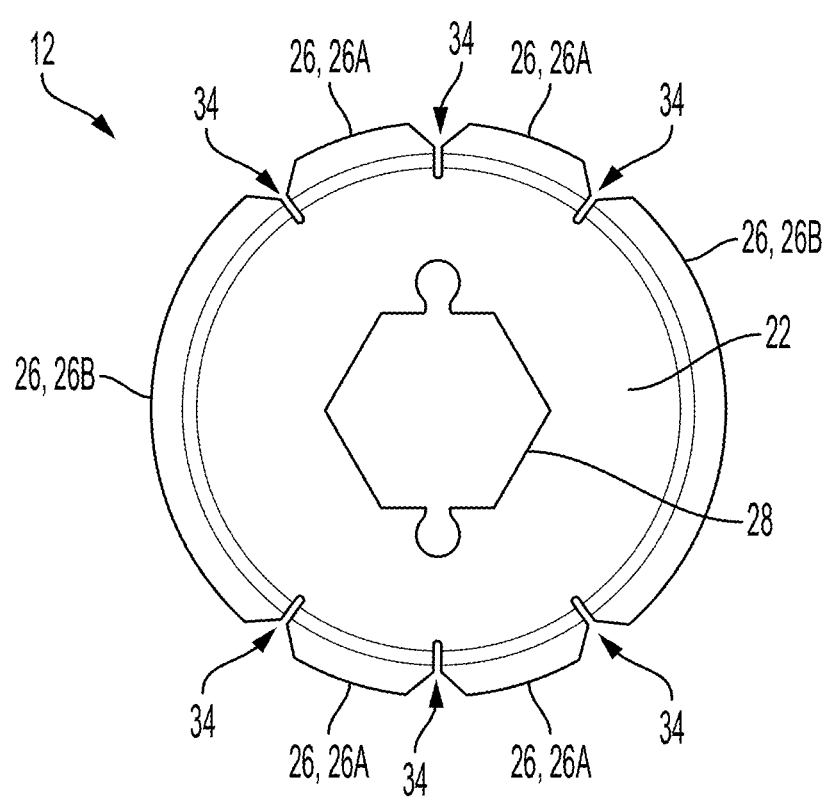
FIG. 3 is a top view of an end cap of the suture cleating system, according to an embodiment.

Turning now to FIG. 3, there is shown a top view of the end cap 12 of the suture cleating system 10, according to an embodiment. As shown, the end cap 12 comprises an outer surface 22. As shown in FIG. 2-3, the outer surface 22 is substantially flat (i.e., planar). In the depicted embodiment, the outer surface 22 is circular to match the circular shape of the seal 16 and proximal end 24 (FIG. 2) of the cannula body 14. The end cap 12 has an aperture 28 extending through the outer surface 22 and one or more cleats 26 extending from the outer surface 22. In FIG. 2, the cleats 26 are projecting pieces of material extending distally from the outer surface 22. In the embodiment shown in FIG. 3, there are two opposing sets of two central cleats 26A between two opposing larger cleats 26B. However, the end cap 12 can be configured such that there is any suitable number of cleats 26.

As shown in FIG. 2, the cleats 26 extend distally from the outer surface 22. It can be seen in both FIGS. 2 and 3 that the cleats 26 extend at angle. In particular, the cleats 26 extend outward at an angle from a central longitudinal y-y axis extending through the suture cleating system 10, as shown in FIG. 2. Referring back to FIG. 3, the end cap 12 has one or more suture slots 34 (or any other kind of opening) between any two cleats 26. The suture slots 34 extend between the cleats 26 and at least partially into the outer surface 22 of the end cap 12. The suture slots 34 in FIG. 3 increase in size distally. In particular, the suture slots 34 are thin and linear through the outer surface 22 of the end cap 12 and open (or increase in size) in a triangular shape distally between the cleats 26.

Figure 1:
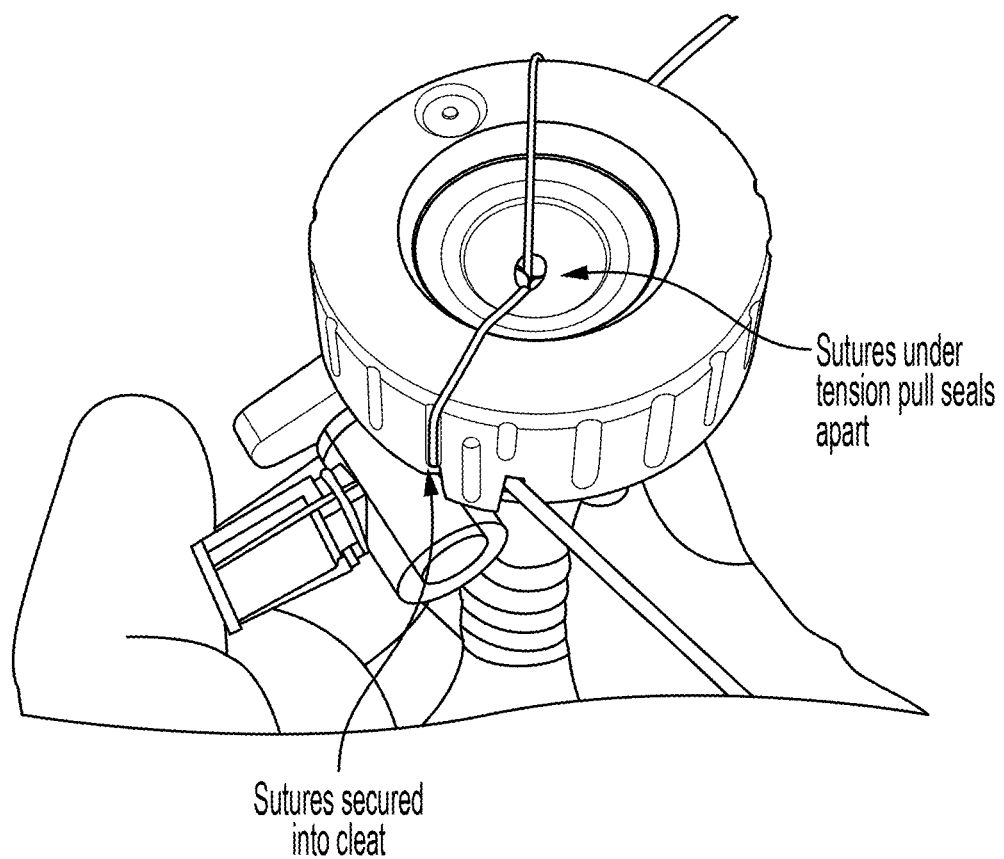
FIG. 1 is a cannula and seal of the prior art.
Figure 4A:
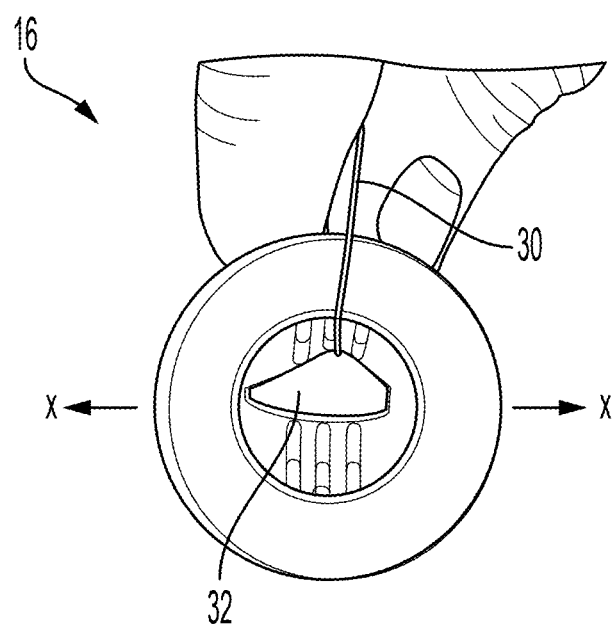
FIG. 4A is a top view of a seal of the suture cleating system, according to an embodiment.
Figure 4B:
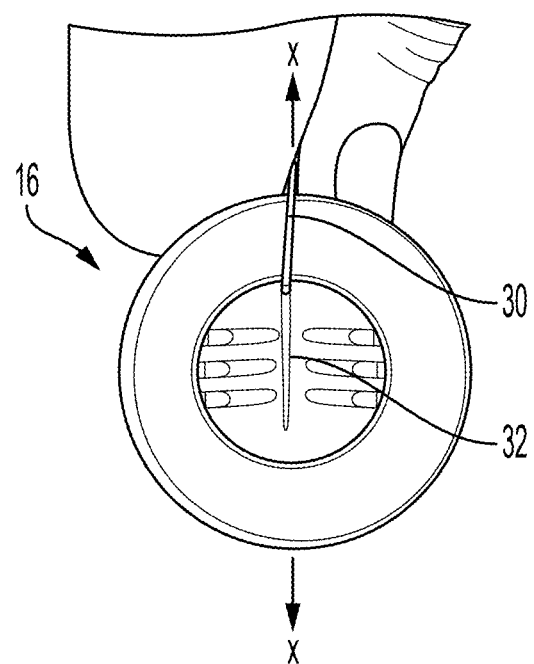
FIG. 4B is a top view of the seal of the suture cleating system, according to an alternative embodiment.

Referring now to FIGS. 4A and 4B, there is shown top views of the seal 16 of the suture cleating system 10, according to embodiments. The seal 16 has a seal slit 32 extending therethrough. In the depicted embodiments, the seal slit 32 is substantially linear and extends substantially across a diameter of the seal 16. Specifically, the seal slit 32 extends along an axis x-x. (The axis x-x is substantially perpendicular to the longitudinal y-y axis, as shown in FIG. 1). The seal slit 32 is wide enough to accommodate suture 30 extending therethrough. The seal 16 in FIGS. 4A-4B is a duckbill or bivalve seal because it is resilient to geometric deformation when the suture 30 is tensioned at a specific angle relative to the orientation of the seal slit 32. However, any other seal design and geometry that is similarly resilient to geometric deformation under the use described below can be used as the seal 16.

According to an exemplary embodiment, in use, a suture 30 is passed through the seal 16 and pulled perpendicular to the length of the seal slit 32, as shown in FIG. 4A. This technique leads to drastic deformation of the seal 16. FIG. 4B shows an alternative exemplary embodiment for passing the suture 30 through the seal 16. As shown in FIG. 4B, the suture 30 is passed through the seal slit 32 and pulled parallel to the length of the seal slit 32. This technique leads to minimal deformation of the seal 16. The difference of deformation between the technique in FIG. 4A and FIG. 4B is apparent when comparing the distorted size of the seal slit 32. The technique in FIG. 4B is preferred to the interaction between the seal 16 and the suture 30 in FIG. 4A because there is minimal deformation, decreasing wear and tear on the seal 16 and increasing its longevity.

Figure 5:
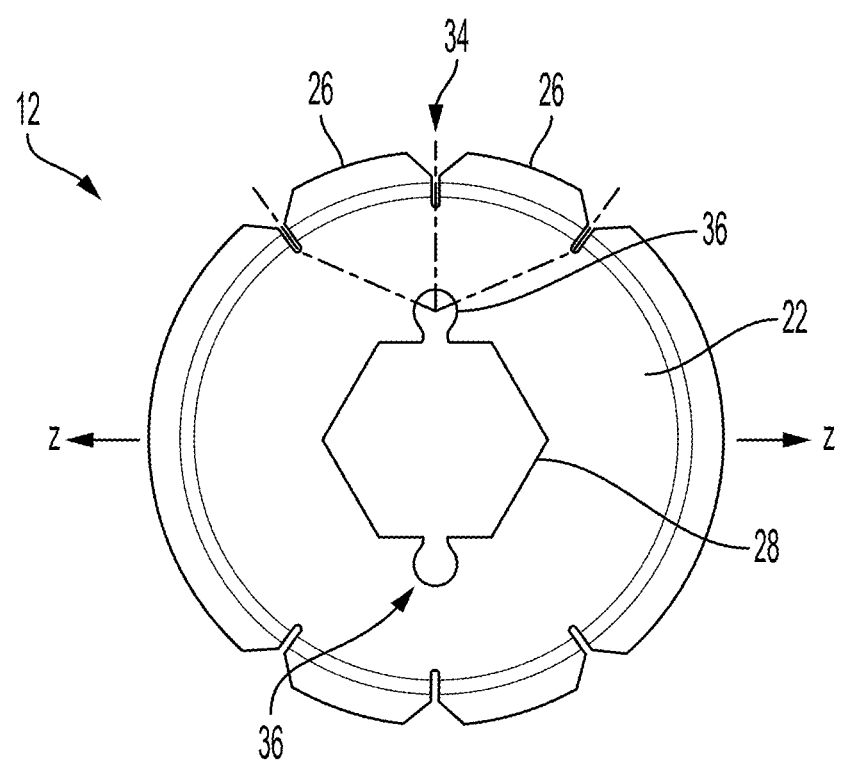
FIG. 5 is a top view of the end cap of the cleating system, according to an embodiment.

Turning now to FIG. 5, there is shown a top view of the end cap 12 of the suture cleating system 10, according to an embodiment. The end cap 12 has one or more suture openings 36. In the depicted embodiment, the end cap 12 has two suture openings 36. As shown in FIG. 5, the suture openings 36 extend from the aperture 28 in the outer surface 22 of the end cap 12. In the embodiment shown, the suture openings 36 are substantially circular or rounded; however, any other geometries may be used for the suture openings 36.

The suture openings 36 can extend at any position from the aperture 28 in the outer surface 22. In FIG. 5, the suture openings 36 extend on opposing sides of the aperture 28. Specifically, in the depicted embodiment, the aperture 28 is hexagon-shaped with the suture openings 36 extending opposite of each other such that the suture openings 36 are mirror images based on an axis z-z axis extending through the hexagon-shaped aperture 28. Using the configuration shown in FIG. 5, the suture 30 is pulled through the aperture 28 and docked in one of the suture openings 36. Then, the suture 30 is locked in one of the cleats 26 by pulling the suture 30 through the suture slot 34 between any two cleats 26, The angle of approach of the suture 30 toward the suture cleat 26 is controlled tightly due to the suture opening 36.

Figure 6:
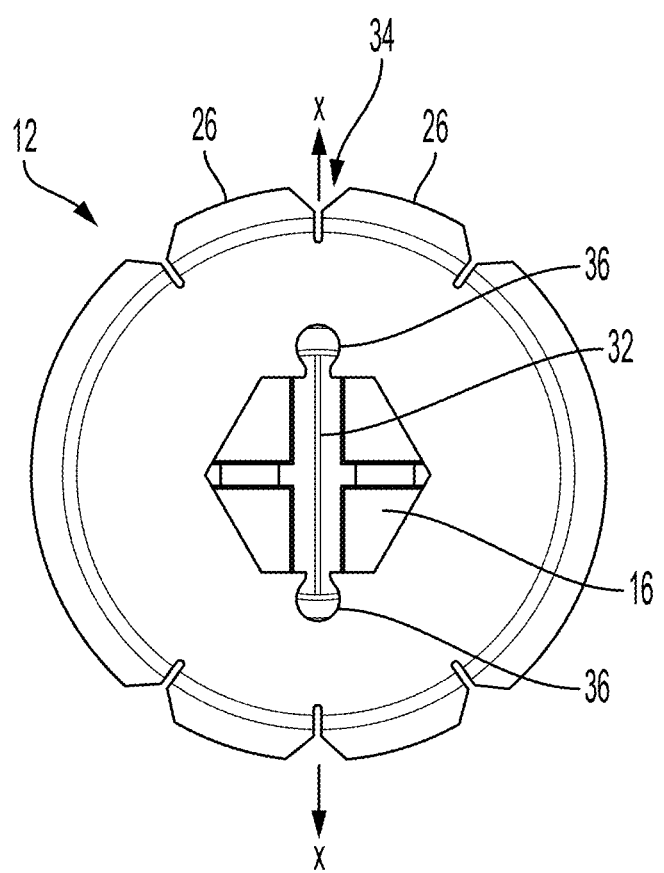
FIG. 6 is a top view of the end cap and seal of the cleating system, according to an embodiment.

Referring now to FIG. 6, there is shown is a top view of the end cap 12 and seal 16 of the cleating system 10, according to an embodiment. As shown in FIG. 6, the seal slit 32 in the seal 16 is aligned with the suture openings 36. Specifically, the axis x-x extending along the length of the seal slit 32 extends between the suture slots 34 (i.e., from one of the suture slots 34 to the other suture slot 34). With the seal slit 32 aligned with the suture slots 34, the suture 30 extending through the seal slit 32 (as depicted in FIG. 4B) is guided into one of the suture openings 36. The suture 30 can then be pulled through one of the adjacent suture slots 34 between two cleats 26. Thus, the suture 30 can be pulled through the seal slit 32 and the suture opening 36 without much, if any, deformation of the seal 16. This allows the suture 30 to be locked under tension while maintaining the functionality of the seal 16, which in turn, prevents fluid leakage and jetting from the cannula.

Figure 7:
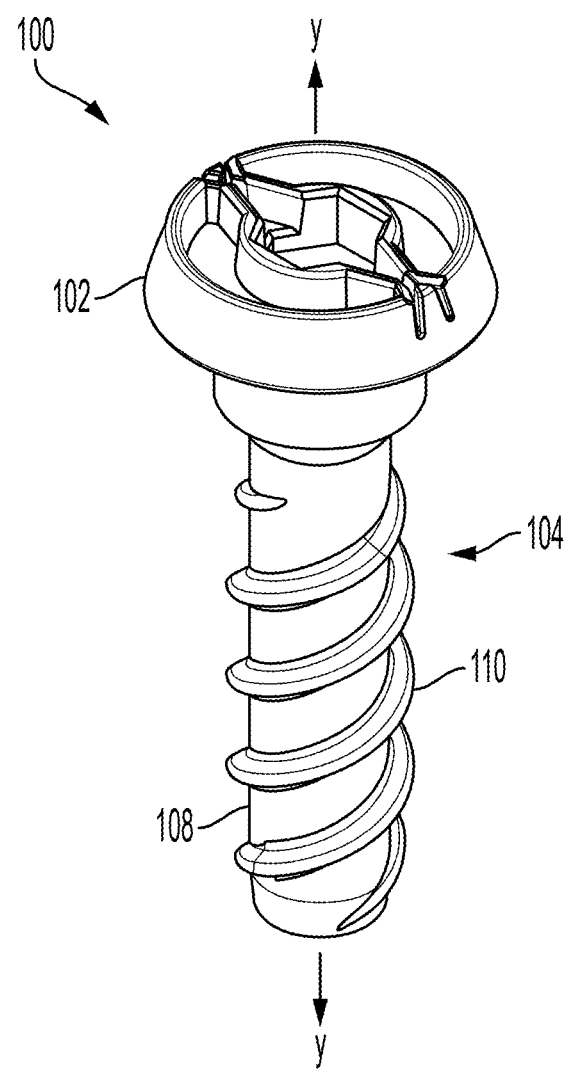
FIG. 7 is a perspective view of a suture cleating system according to an alternative embodiment.
Figure 8:
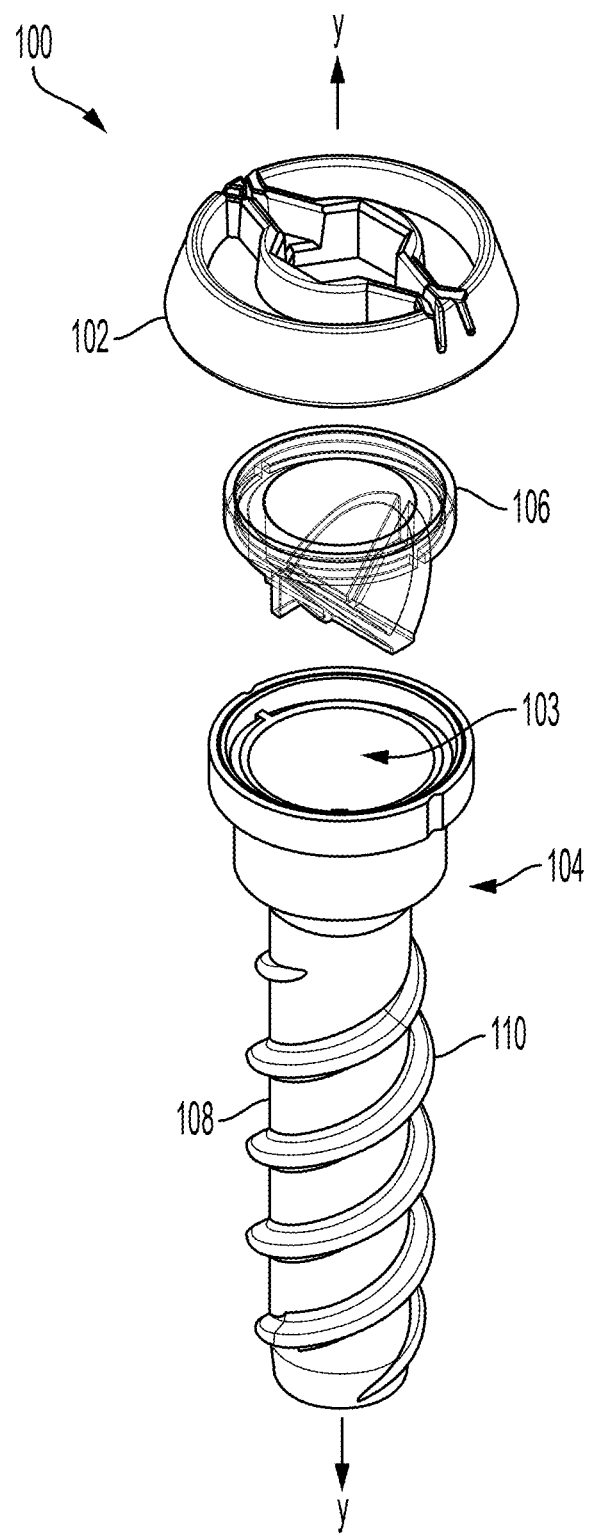
FIG. 8 is an exploded view of the suture cleating system, according to an alternative embodiment.

Turning now to FIGS. 7-13, there are shown various views of a suture cleating system 100, according to an alternative embodiment. FIGS. 7 and 8 show a perspective view and an exploded view, respectively, of an alternative embodiment of the suture cleating system 100. The suture cleating system 100 includes a proximal end cap 102 with a cannula body 104 extending therefrom. A seal 106 (FIG. 8) is positioned between the end cap 102 and the cannula body 104. The cannula body 104 is a tube 108 with an inner volume 103 (FIG. 8) extending therethrough. As shown, the cannula body 104 has threads 110 extending along at least a portion of the tube 108.

Figure 9:
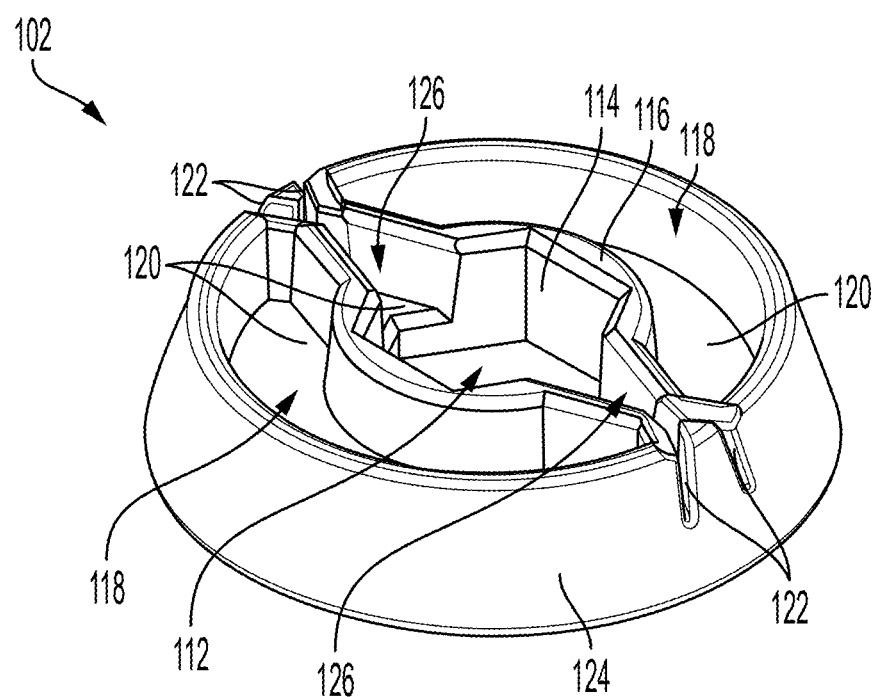
FIG. 9 is a perspective view of an end cap of the suture cleating system, according to an alternative embodiment.

Turning now to FIG. 9, there is shown a perspective view of the end cap 102 of the suture cleating system 100, according to an alternative embodiment. As shown, the end cap 102 comprises an aperture 112 extending therethrough. In the depicted embodiment, the aperture 112 is a wide hexagonal opening. Boundaries defining the aperture 112 are interior walls 114 of the end cap 102. Ends 116 of the interior walls 114 are chamfered or angled to facilitate insertion of an object (e.g., a graft) into the cannula body 104.

The hexagonal geometry of the aperture 112 allows the end cap 102 to engage with a corresponding hexagonal geometry of a proximal obturator (not shown). During assembly or manufacture of the suture cleating system 100, the end cap 102 is attached to the cannula body 104 via sonic welding. The end cap 102 has recesses 118 (i.e., negative space) that allows for the sonic welding horn to reach a bottom surface 120 of the end cap 102 and thus allows for near field sonic welding which bonds the end cap 102 to the cannula body 104.

Figure 11:
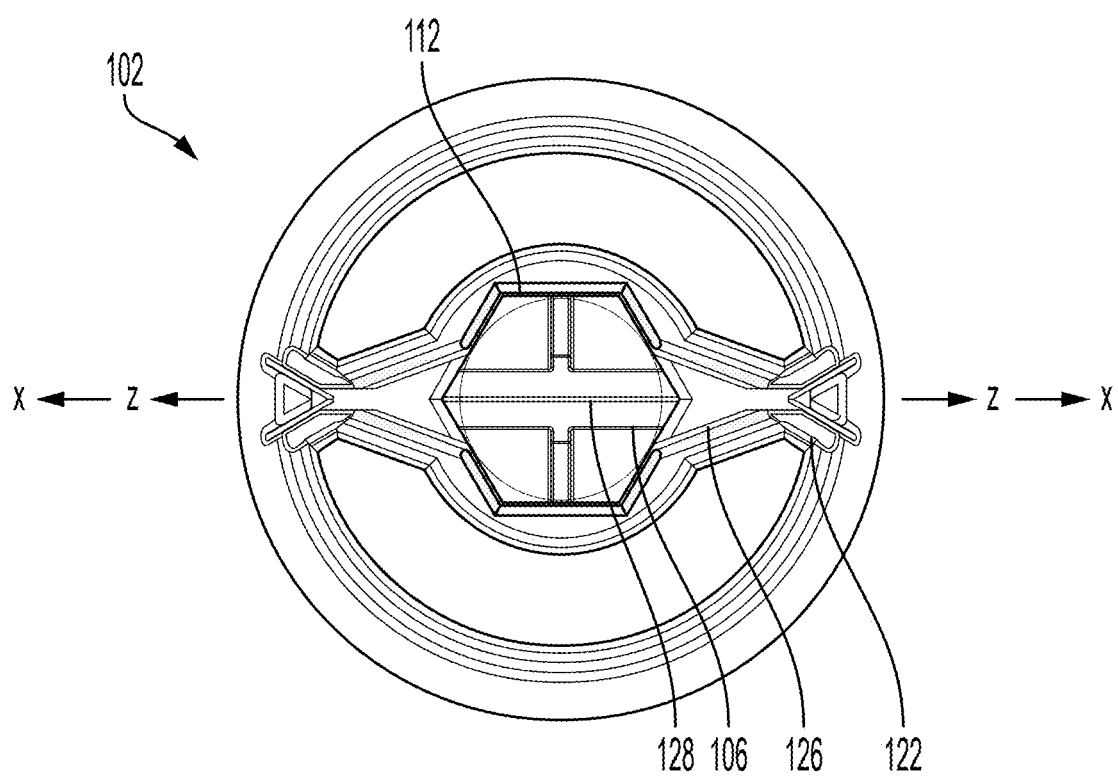
FIG. 11 is a top view of the suture cleating system, according to an alternative embodiment.

Still referring to FIG. 9, there are one or more suture slots 122 extending from the aperture 112 and through the end cap 102. Specifically, the end cap 102 comprises an outer surface 124 and the one or more suture slots 122 extend through the outer surface 124 of the end cap 102. In the embodiment shown in FIG. 9, the end cap 102 has four suture slots 122. The suture slots 122 are created between any two walls 114 of the end cap 102. The walls 114 function like the cleats 26 (i.e., protrusions) in FIGS. 3 and 6 above. Thus, the end cap 102 in FIG. 9 has cleats 26. The four suture slots 122 are arranged such that two suture slats 122 converge within the end cap 102 and the other two suture slots 122 converge within the end cap 102. The two sets of two suture slots 122 oppose each other such that the end cap 102 has mirror symmetry along an axis z-z (FIG. 11). Each of the two sets of two suture slots 122 extend to a triangle recess 126 that extends to the aperture 112. The triangular recesses 126 extend to the bottom surface 120 of the end cap 102.

The configuration of the suture slots 122 described above allows the user to cleat one or more sutures on the end cap 102 by pushing a suture into at least one of the suture slots 122 and past the outer surface 124 of the end cap 102, securing the suture. In prior art systems, users must reach under the end cap to access the suture cleat, which can be difficult to locate when looking straight down onto the end cap. Thus, the suture cleating system 100 described herein provides a user with increased visibility and control of the suture.

Figure 10:
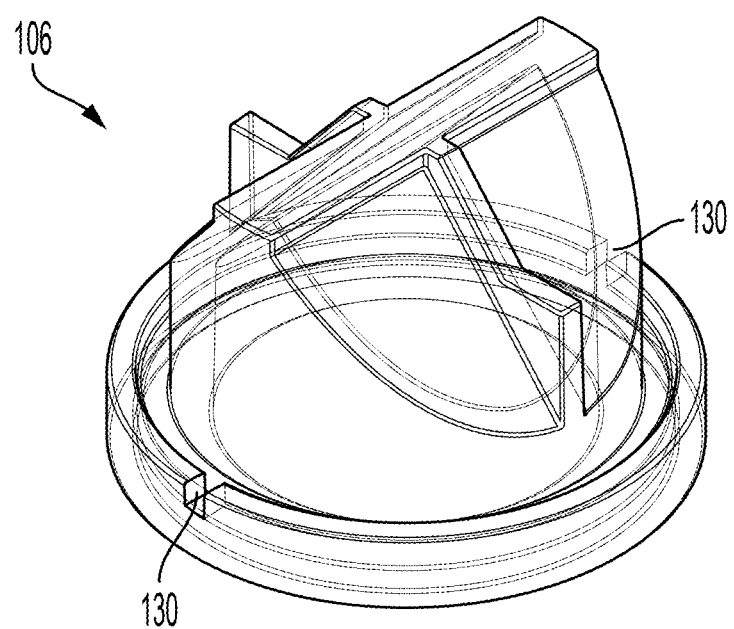
FIG. 10 is a perspective view of a seal of the suture cleating system, according to an alternative embodiment.

Referring now to FIG. 10, there is shown a perspective view of the seal 106 of the suture cleating system 100, according to an alternative embodiment. The seal 106 in the depicted embodiment is a duckbill-styled seal. The seal 106 has a seal slit 128 which extends at least partially across a diameter of the seal 106 (as described and shown in the embodiment in FIGS. 1-6 above). The seal slit 128 extends along an axis x-x (FIG. 11). The seal 106 has features that interface with the end cap 102 and the cannula body 104. For example, the seal 106 has one or more colinear notches 130 that are used to align the seal 106 in the correct orientation with respect to the end cap 102.

Turning now to FIG. 11, there is shown a top view of the suture cleating system 100, according to an alternative embodiment. As shown, a seal slit 128 of the seal 106 is aligned with the aperture 112 of the end cap 102. The seal slit 128 is aligned with the aperture 112 such that the axis x-x extending along the seal slit 128 extends between the convergence of the suture slots 122 (and extends between the triangular recesses 126). In other words, the axis x-x is substantially aligned with the axis z-z. When the suture extends through the seal 106 (via the seal slit 128) and is cleated (i.e., placed within a suture slot 122), the triangular recess 126 keeps the suture horizontal, thus keeping the seal 106 closed. If the suture were to be pulled vertically, the seal 106 would be forced open and deformed.

Figure 12:
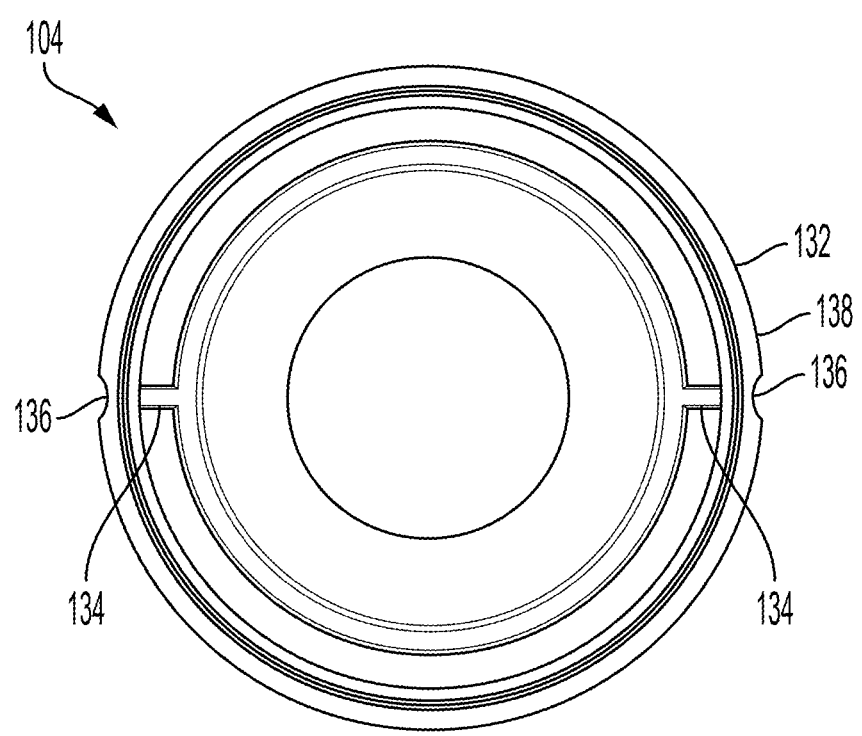
FIG. 12 is a top view of the cannula body of the suture cleating system, according to an alternative embodiment.

Referring now to FIG. 12, there is shown a top view of the cannula body 104 of the suture cleating system 100, according to an alternative embodiment. A proximal end 132 of the cannula body 104 comprises alignment features for attachment to the seal 106 and the end cap 102. For example, the proximal end 132 of the cannula body 104 has colinear notches 134 for receiving notch features of the seal 106 and/or end cap 102. The proximal end 132 of the cannula body 104 may also include colinear grooves 136 in an outer surface 138 of the cannula body 104 for connection to the seal 106 and/or end cap 102.

Figure 13:
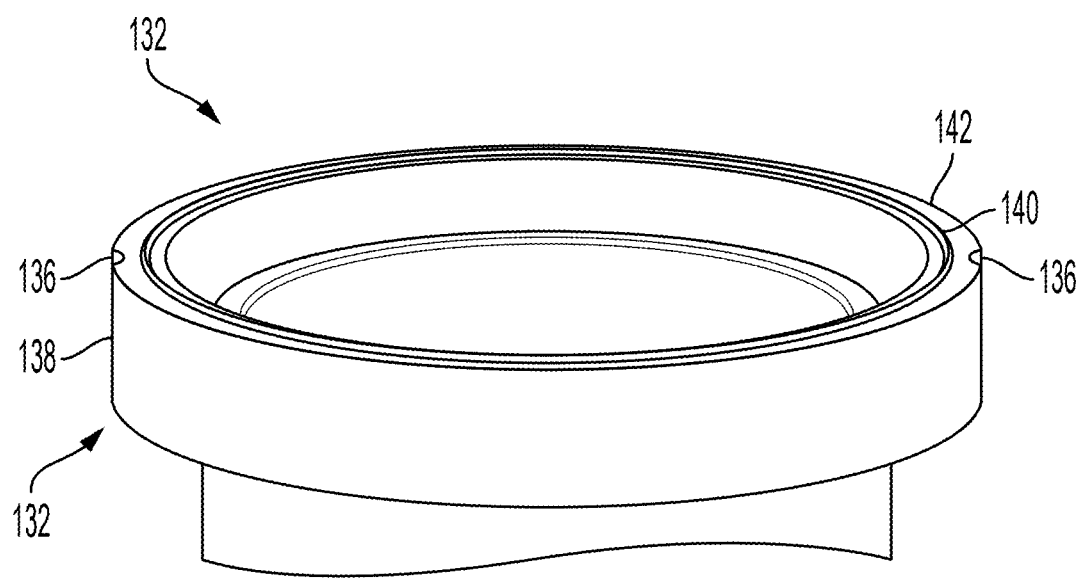
FIG. 13 is a close-up, elevated side view of the cannula body of the suture cleating system, according to an alternative embodiment.

Turning now to FIG. 13, there is shown a close-up, elevated side view of the cannula body 104 of the suture cleating system 100, according to an alternative embodiment. The proximal end 132 of the cannula body 104 has a triangular-shaped energy director 140 that runs all around a top surface 142 of the proximal end 132 of the cannula body 104. In the depicted embodiment, the energy director 140 is a channel that runs along the top surface 142 in a circular, creating an interior circumference. Upon sonic welding, the energy director 140 will fill out the top surface 142, creating an even and strong bond.

It should be understood that the values used above are only representative values, and other values may be in keeping with the spirit and intention of this disclosure.

While several inventive embodiments have been described and illustrated herein with reference to certain exemplary embodiments, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein (and it will be understood by one skilled in the art that various changes in detail may be effected therein without departing from the spirit and scope of the invention as defined by claims that can be supported by the written description and drawings). More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Further, where exemplary embodiments are described with reference to a certain number of elements it will be understood that the exemplary embodiments can be practiced utilizing either less than or more than the certain number of elements.

All references, including publications, patent applications, and patents, cited herein are hereby incorporated by reference to the same extent as if each reference were individually and specifically indicated to be incorporated by reference and were set forth in its entirety herein.

All definitions, as defined and used herein, should be understood to control over dictionary definitions, definitions in documents incorporated by reference, and/or ordinary meanings of the defined terms.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if not directly attached to where there is something intervening.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A suture cleating system, comprising:
   an end cap comprising an outer surface with an aperture extending therethrough and one or more cleats extending therefrom;
   a seal connected to the end cap, the seal having a seal slit extending at least partially across its diameter;
   wherein the seal slit is substantially aligned with the aperture of the end cap; and
   wherein the aperture is hexagonal with two opposing triangular recesses extending therefrom, each of the two opposing triangular recesses extending to two converging suture slots positioned on the outer surface of the end cap.

2. The system of claim 1, wherein the two opposing triangular recesses extend through the outer surface.

3. The system of claim 1, wherein the one or more cleats extend distally from the outer surface at angle.

4. The system of claim 1, wherein the two converging suture slots are positioned between two of the one or more cleats.

5. The system of claim 4, wherein the two converging suture slots extends at least partially through the outer surface.

6. The system of claim 1, wherein each of the one or more cleats is a wall of the end cap.

7. The system of claim 1, wherein each of the two converging suture slots extend between two of the one or more cleats.

8. The system of claim 1, wherein the seal slit is colinear with the two opposing triangular recesses.

9. A suture cleating system, comprising:
   an end cap comprising an aperture extending therethrough and one or more cleats extending therefrom;
   a cannula body extending distally from the end cap;
   a seal connected between the cannula body and the end cap, the seal having a seal slit extending therethrough;
   wherein the seal slit is substantially aligned with the aperture of the end cap; and
   wherein the aperture is hexagonal with two opposing triangular recesses extending therefrom, each of the two opposing triangular recesses extending to two converging suture slots positioned on the end cap.

10. The system of claim 9, wherein the seal slit extends at least partially across a diameter of the seal.

11. The system of claim 9, wherein the cannula body comprises a tube with threads extending along at least a portion thereof.

12. The system of claim 9, wherein the two converging suture slots are positioned between two of the one or more cleats.

13. The system of claim 9, further comprising a suture extending through the seal slit and the aperture.

14. The system of claim 13, wherein the suture extends from the aperture and through one of the two converging suture slots positioned between two of the one or more cleats.

15. The system of claim 13, wherein the suture extends from one of the two opposing triangular recesses to one of the two converging suture slots.

16. The system of claim 9, wherein each of the two converging suture slots extend between two of the one or more cleats.

17. The system of claim 9, wherein the seal slit is colinear with the two opposing triangular recesses.

* * * * *